United States Patent [19]

Nazzaro-Porro

[11] 4,292,326
[45] Sep. 29, 1981

[54] PROCESS FOR TREATMENT OF HYPERPIGMENTARY DERMATOSES

[76] Inventor: Marcella Nazzaro-Porro, Via Viminale 38, Rome, Italy

[21] Appl. No.: 965,584

[22] Filed: Dec. 1, 1978

Related U.S. Application Data

[63] Continuation-in-part of Ser. No. 895,565, Apr. 12, 1978, abandoned.

[30] Foreign Application Priority Data

Dec. 30, 1977 [IT] Italy ............................... 31471 A/77

[51] Int. Cl.³ ............................................. A61K 31/19
[52] U.S. Cl. ..................................... 424/317; 562/594
[58] Field of Search ................. 424/317; 562/590, 594

[56] References Cited

U.S. PATENT DOCUMENTS 2,402,639  6/1946  Lazier et al. .................... 562/594 X
2,581,514  1/1952  Chilcotte ............................ 562/594
2,602,815  7/1952  Gregory et al. ................ 562/594 X
2,657,231 10/1953  Klarer et al. ................... 562/594 X
2,729,675  1/1956  Cowen ................................ 562/594
3,066,077 11/1962  De Mytt ......................... 562/594 X

OTHER PUBLICATIONS

Porro et al., Gior. e Min. Derm., pp. 207–209 (B–1977).
Chemical Abstracts 66:1860e (1967).
Chemical Abstracts T4:16659(c) (1960).
"Malignant Melanoma", Kopf et al., Mason Pub., 1979, p. 7.

Primary Examiner—Leonard Schenkman
Attorney, Agent, or Firm—Roylance, Abrams, Berdo & Farley

[57] ABSTRACT

There is disclosed a composition for the treatment of acne, hyperpigmentary dermatoses or skin hyperpigmentation which contains dicarboxylic acids containing 7 to 13 carbon atoms or certain derivatives thereof that contain reducing functional group or a salt thereof. There are also disclosed methods for preparing mercapto derivatives of these dicarboxylic acids.

9 Claims, No Drawings

PROCESS FOR TREATMENT OF HYPERPIGMENTARY DERMATOSES

This application is a continuation-in-part of my application Ser. No. 895,565, filed Apr. 12, 1978, now abandoned.

This invention relates to compositions for the treatment of acne, hyperpigmentary dermatoses and the like.

Acne is a widespread skin ailment which comprises an abnormal condition affecting chiefly the skin of the face (but also that of the shoulders and chest), characterized by the development of pimples, blackheads, and pustules, and caused by an infection and inflammation of the wax-producing (sebaceous) glands. The most common form is known as acne vularis and occurs cheifly in young people between the ages of 12 or 13 and 20. It is believed that the initiating cause of acne is a temporary abnormality in the activity of certain glands, especially the sex glands (which in the early teen years become highly functional and sometimes unstable) and the glands concerned with growth. Emotional upheavals, which upset the glandular balance and normal function, also result in an outbreak of acne.

Dermatoses, such as skin hyperpigmentations (which frequently produce a disfiguring effect, such as in the case of chloasma of the face), constitute a problem not only of an esthetic but also of a therapeutic nature, for which as yet no basic solution has been found. Only hydroquinone and its derivatives have up to now shown some effectiveness, in vivo, for the treatment of skin hyperpigmentations. However, they cause as a side effect, the development of long-lasting hypopigmented zones, which are at times irreducible. An object of the present invention is to provide compositions which are useful for normalizing the color of skin effected by non-cancerous or non-precancerous hyperpigmentation.

The compositions encompassed in the present invention are characterized by the fact that they contain as active ingredients a dicarboxylic acid having from 7 to 13 carbon atoms or a derivative thereof containing at least one reducing group in the molecule or a salt thereof. These compositions which can be applied topically in the form of creams, ointments, unguents, and lotions, are characterized therefore by the fact that they contain a dicarboxylic acid preferably selected from the group consisting of pimelic, suberic, azelaic, sebacic, 1,9-nonanedicarboxylic, 1,10-decanedicarboxylic, and 1,11-undecanedicarboxylic acids or derivatives of such acids containing a reducing functional group, preferably a mercapto derivative or a salt thereof. The compositions of the present invention have been found in particular capable of inhibiting the formation of the skin pigment (melanin) by blocking the dopa-tyrosinase reaction by a competitive type mechanism. The compositions have also been found to be useful in the treatment of acne.

Without desiring to establish any limitations for the scope of the present invention and without trying to give a binding explanation of the mechanism of action of the active component of the compositions of the present invention in the treatment of dermatoses, it seems plausible to seek the cause of their activity in a mechanism similar to that encountered in the experimental studies carried out by the applicant on the behavior of a fungus, *Pityrosporum orbiculare*, which is the cause of a dermatosis which manifests itself by the appearance of achromic or whitish flecks or spots (*Pityriasi versicolor*). From observations carried out in vitro and in vivo of the behavior of this fungus it is reasonable to believe that, by metabolizing the fatty acids normally present on the skin and necessary for their survival and diffusion, this fungus causes the formation of the said dicarboxylic acids, which are specifically responsible for the subsequent effect of inhibiting melano-genesis.

In this respect, it should be noted that from an examination of cultures of *Pityrosporum orbiculare*, to which technical oleic acid was added as lipid supplement after saponification there was also found the presence of pimelic, azelaic, and 1,9-non-andicarboxylic ($C_{11}$) acids, identified by gas chromatography and mass spectrometry. The $C_9$ and $C_{11}$ members of the series of dicarboxylic acids have shown, in vitro, a substantial anti-tyrosinase activity, which has furthermore been encountered also in the members having 8, 10, 12 and 13 carbon atoms.

From a study of the mechanism of action of the above indicated acids it has furthermore been possible to formulate and synthesize derivatives having a better action in inhibiting the dopa-tyrosinase reaction, the main ones of which are the mercapto derivatives. Therefore, another feature of the present invention concerns the derivatives of dicarboxylic acids or their salts having from 7 to 13 carbon atoms in their molecule and characterized by the fact that they contain at least one reducing group, preferably a mercapto group.

The dicarboxylic acids, their derivatives or salts described above may be applied in a variety of pharmaceutically acceptable vehicles which would depend on the mode of treatment. Thus, for example, they may be used in the form of an injectable suspension of the active material in saline solution. On the other hand, if they are intended for topical application, they may be applied in creams. Moreover, they may be given in orally administerable form. The quantity of active ingredient that will be contained in these compositions may vary somewhat. All that is required is that the dicarboxylic acids or their derivatives or salts thereof be present in therapeutically effective amounts. The quantity of dicarboxylic acid or its derivatives or salts thereof that will be contained in the composition of this invention will vary depending upon the dosage form and/or the condition treated. Thus, for example, when given orally they may comprise all or substantially all of the dosage forms. On the other hand, when contained in a dosage form suitable for subcutaneous injection they may comprise between about 20% to 30% by weight, and preferably about 25% by weight based on the total weight of the composition. In case the composition takes the form of a cream or lotion suitable for topical application, the dicarboxylic acid or its derivatives or salts thereof may constitute between about 10% to 20% by weight and preferably about 15% by weight based on the total weight of the composition.

It has also been found to be advantageous to include a keratolytic agent in the compositions of this invention. This is particularly the case when the compositions are intended to be applied to the skin. By way of example of the keratolytic agents that may be employed herein, mention may be made of salicylic acid, vitamin A acid, resorcinol, phenol, cresol, etc. The quantity of keratolytic agent that can advantageously be employed herein also varies. Ordinarily, this will constitute from about 2% to about 4% by weight based on the total weight of the composition.

The following examples are given to further illustrate the present invwntion without constituting any undue limitation thereon.

EXAMPLE 1

(a) Preparation of the Alpha-Monobromo Derivative 1 mole of dicarboxylic acid (for instance, azelaic acid) is introduced into a 3 liter flask placed on a magnetic agitator provided with a heating plate, and 500 g of phosphorous pentachloride are added. After the reaction has taken place (complete melting), 60 ml of anhydrous bromine are added in small portions in the course of about 6 hours, with continuous agitation. The reaction temperature is maintained at 60° to 70° C.

After the reaction is complete, it is cooled and thereupon about 500 ml of distilled water are cautiously added; it is then warmed on the magnetic agitator for about 30 minutes and cooled.

The low organic phase, formed of an oily liquid of dark yellow color, constitutes the crude monobromo derivative which is distilled under vacuum.

(b) Preparation of the Mercapto Derivative 1 mole of alpha-monobromo derivative is introduced, under a hood, into a 2 liter flask provided with a condenser thereupon 50 ml of ethyl alcohol are added at 95° C. and 1.1 mole of thiourea. The mixture is brought to a boil for 6 hours, whereupon the alkyl thiouronium salt is separated out by cooling.

For the saponification of this salt, 500 ml of 5 N NaOH are added to the mixture and it is boiled under reflux for an additional two hours. The reaction mixture, after being cooled, is acidified with 5 N HCl and, after agitation for about 10 minutes, an oily layer forms, which is removed. The aqueous layer is extracted 3 times with ethyl ether, and this ether extract is added to the oily layer which was previously removed, which was then dried over anhydrous $Na_2SO_4$. After removal of the ether by distillation, the crude mercapto derivative is purified in a column containing silica gel.

For the preparation of dimercapto derivatives, the procedure of the preceding example is repeated with the following differences:

1. The dibromo derivative of the dicarboxylic acid is prepared in the same manner as the monobromo derivative, but doubling the amount of bromine added and tripling the reaction times; the reaction temperature is maintained at 90° to 100° C.

2. During the phase of preparation of the mercapto derivative, twice the quantities of alcohol, thiourea, and soda respectively are used for each mole of dibromide.

In order to evaluate the activity of the compositions in accordance with the present invention, and therefore of the respective active ingredients, pharmacological studies were carried out as well as tests in vivo.

From the combined lipid extracts (cellular and from the filtrate) of cultures of *Pityrosporum orbiculare* (strain 4709) grown for 20–30 days on a conventional synthetic medium to which oleic acid was added, there was obtained a saponifiable portion having substantial activity in inhibiting tyrosinase. Subjecting this portion to thin layer chromatography (TLC), a fraction was isolated, of Rf=0.13, capable of inhibiting the dopa-tyrosinase reaction.

Analysis by gas chromatography and subsequent analyses by mass spectrometry have shown the presence in this fraction of a series of $C_5$–$C_9$ dicarboxylic acids with a quantitative predominance of pimelic and azelaic acids.

From a comparative test using samples of pure acids, it has been possible to exclude any tyrosinase inhibiting activity on the part of glutaric acid ($C_5$) while such activity becomes evident starting with the $C_7$ member, and is a maximum for the $C_9$ and $C_{11}$ members.

In particular, enzymatic kinetics tests have shown that azelaic acid is a competitive inhibitor of tyrosinase with a $Ki = 4.10^{-4}$ M.

EXAMPLE 2

The in vivo applications of the compositions of the present invention are illustrated by the following experiments:

A cream having a base of azelaic acid (see Examples 3–5 below) was applied for 30 days to the dark spots on the following patients:

(a) 20 patients suffering from chloasma
(b) 3 patients suffering from poikiloderma of Civatte All the patients, at the end of the treatment, showed a clear lightening of the hyperpigmented zones, and in most cases, there was obtained an apparently complete cure without collateral effects. After five months of observation, none of the patients treated showed any traces of leukoderma. The general condition of the skin was improved especially in those patients affected with acne.

Examples 3–5 below are exemplary of cream compositions that are used in the procedure described in Example 2 above.

EXAMPLE 3

| | % by Wt. |
|---|---|
| Azelaic acid | 15.0 |
| Chlorocresol | 0.1 |
| Titanium dioxide | 1.0 |
| Salicylic acid | 2.0 |
| Glycerol monostearate | 2.0 |
| Cetyl alcohol | 3.0 |
| Tween 80 | 5.0 |
| Sodium laurylethersulfate | 10.0 |
| Ethanolamine laurylether sulfate | 1.0 |
| Olive oil | 2.0 |
| Vitamin C | 1.0 |
| Distilled water to | 100% |

EXAMPLE 4

Same as Example 3, except salicylic acid is used at a 3% level.

EXAMPLE 5

Same as Example 3, except that salicylic acid is used at 4% level.

EXAMPLE 6

The following composition is suitable for use for subcutaneous injection of alpha-mercapto azelaic acid:

| | |
|---|---|
| Alpha-monomercapto-azelaic acid | 2 mg |
| Tween 80 | 5 mg |
| Vitamin C | 1 mg |

EXAMPLE 7

A cream having a base of azelaic acid (see Examples 3–5 above) was applied twice a day for two months on 10 women, aged 20–24, with chloasma and a mild form of acne (comedones, pustules, papules, nodules). Three of the cases were affected with a chronic premenstrual form of acne confined to the chin. Following the two months of treatment, all patients were very much improved, both as respects chloasma and acne.

EXAMPLE 8

A cream as described in Example 7 was used to treat 10 cases of acne vulgaris (six males and four females, aged 16–25) of different degrees of severity. It was observed that the postules dry very early (1–2 days), that the nodules become rapidly flat with disappearance of inflammatory reaction and formation of a crust in 4–6 days and that the lesions recover without formation of scars. After two months of treatment, all of the patients were improved. This therapy has been especially useful in those patients with severe forms of acne which did not tolerate a general therapy with antibiotics.

EXAMPLE 9

The cream described in Example 7 was used to treat three girls aged 15–18 afflicted with a non-inflammatory form of acne mainly represented by closed comedones (whiteheads). The patients appeared to be cured of their affliction following 3–4 months of application of the cream.

In the practice of this invention in the treatment of acne, at the beginning of the therapy and also during the course of treatment in the case of inflamed lesions, patients experience a transient itching and burning and the skin appears slightly red and scaly.

What is claimed is:

1. A method for the treatment of individuals exhibiting noncancerous or non-precancerous hyperpigmentary dermatoses which comprises administering to said individual a therapeutically effective amount of an active ingredient in a pharmaceutically acceptable carrier until said condition is reduced or its further development is arrested wherein said active ingredient is at least one dicarboxylic acid containing from 7 to 13 carbon atoms or a mono or dimercapto derivative of said acid or a salt thereof.

2. A method as defined in claim 1 wherein said dicarboxylic acid is selected from the group consisting of pimelic acid, suberic acid, sebacic acid, azelaic acid, 1,9-nonanedicarboxylic acid, 1,10-decanedicarboxylic acid, and 1,11-undecanedicarboxylic acid.

3. A method as defined in claim 1 wherein said individual exhibits a chloasma condition.

4. A method as defined in claim 1 wherein said individual exhibits a poikiloderma of Civatte condition.

5. A method as defined in claim 1 wherein said acid is administered orally.

6. A method as defined in claim 1 wherein said acid is administered by injection.

7. A method as defined in claim 1 wherein said acid is administered topically.

8. A method as defined in claim 1 wherein said dicarboxylic acid is azelaic acid.

9. A method as defined in claim 1 wherein said dicarboxylic acid is 1,10-decanedicarboxylic acid.

* * * * *